(12) United States Patent
Schlesinger et al.

(10) Patent No.: US 8,989,839 B2
(45) Date of Patent: Mar. 24, 2015

(54) METHOD AND APPARATUS FOR DIAGNOSIS OF TUMOR ACTIVITY USING TUMOR INTERSTITIAL FLUID PRESSURE

(75) Inventors: Mordechay Schlesinger, Windsor (CA); Long Jian Liu, Windsor (CA); James R. Ewing, Detroit, MI (US); Stephen L. Brown, Detroit, MI (US)

(73) Assignees: University of Windsor, Windor, Ontario (CA); Henry Ford Hospital, Detroit, MI (US)

( * ) Notice: Subject to any disclaimer, the term of this patent is extended or adjusted under 35 U.S.C. 154(b) by 35 days.

(21) Appl. No.: 13/585,784

(22) Filed: Aug. 14, 2012

(65) Prior Publication Data

US 2014/0051981 A1    Feb. 20, 2014

(51) Int. Cl.
*A61B 5/03* (2006.01)
*A61B 5/055* (2006.01)
*A61B 5/00* (2006.01)

(52) U.S. Cl.
CPC ................. *A61B 5/03* (2013.01); *A61B 5/0059* (2013.01)
USPC ............................ 600/420; 600/431; 600/425

(58) Field of Classification Search
USPC .................... 600/411, 419, 420, 431; 424/9.1
See application file for complete search history.

(56) References Cited

U.S. PATENT DOCUMENTS

2009/0264734 A1 * 10/2009 Degani et al. ................. 600/420

OTHER PUBLICATIONS

Liu, L, et al. "Phenomenological model of interstitial fluid pressure in a solid tumor" Physical Review E 84, 021919 (2011).*
L. J. Liu, et al., "Phenomenological model of interstitial fluid pressure in a solid tumor", Physical Review E, vol. 84, pp. 021919-1-021919-9, (2011).
S. Ferretti, et al., "Tumor Interstitial Fluid Pressure as an Early-Response Marker for Anticancer Therapeutics", Neoplasia, vol. 11, No. 9, pp. 874-881, (Sep. 2009).
Alexei V. Salnikov, et al., "Lowering of tumor interstitial fluid pressure specifically augments efficacy of chemotherapy", The FASEB Journal, vol. 17, pp. 1756-1758, (Sep. 2003).
Sarah Jane Lunt, et al., "Interstitial fluid pressure, vascularity and metastasis in ectopic, orthotopic and spontaneous tumors", BMC Cancer, vol. 8, No. 2, 14 pgs., (2008).
Einar K. Rofstad, et al., "Associations between Radiocurability and Interstitial Fluid Pressure in Human Tumor Xenografts without Hypoxic Tissue", Clinical Cancer Research, vol. 16, No. 3, pp. 936-945, (Feb. 1, 2010).
Seung-Gu Yeo, et al., "Interstitial Fluid Pressure as a Prognostic Factor in Cervical Cancer Following Radiation Therapy", Clinical Cancer Research, vol. 15, No. 19, pp. 6201-6207, (Oct. 1, 2009).

(Continued)

*Primary Examiner* — Michael Rozanski
(74) *Attorney, Agent, or Firm* — Blakely, Sokoloff, Taylor & Zafman LLP

(57) ABSTRACT

A scanning apparatus, is used to effect multiple images of a tumor in which a contrast agent has been localized as a detectable marker over a selected time to map the change in the imaged marker. The rate of change in the imaged marker and/or contrast intensity of the dyed tissues is used to assess tumor aggressiveness and as an early predictor of response to cancer therapy. In particular, following the marking of tumor or cancerous tissues by the initial localization of an imageable contrast agent, the rate of change in the volume and/or area of the imaged marker is used to provide an indication of tumor interstitial fluid pressure (TIFP).

18 Claims, 2 Drawing Sheets

(56) References Cited

OTHER PUBLICATIONS

Terence P.F. Gade, et al., "Imaging Intratumoral Convection: Pressure-Dependent Enhancement in Chemotherapeutic Delivery to Solid Tumors", Clinical Cancer Research, vol. 15, No. 1, pp. 247-255, (Jan. 1, 2009).

Yves Boucher, et al., "Interstitial Pressure Gradients in Tissue-Isolated and Subcutaneous Tumors: Implications for Therapy", Cancer Research, vol. 50, pp. 4478-4484, (Aug. 1, 1990).

Eric J. Hall, et al., "Section I—Chapter 6—Oxygen Effect and Reoxygenation", Radiobiology for the Radiologist, $6^{th}$ Edition, Lippincott Williams & Wilkins, Philadelphia, PA, pp. 90-103, (2006).

F. Stuart Foster, et al., "Ultrasound for the visualization and quantification of tumor microcirculation", Cancer and Metastasis Reviews, vol. 19, pp. 131-138, (2000).

Adrianus J. De Langen, et al., "Use of $H_2^{15}O$-PET and DCE-MRI to Measure Tumor Blood Flow", The Oncologist, vol. 13, pp. 631-644, (2008).

Laurence T. Baxter, et al., "Transport of Fluid and Macromolecules in Tumors I. Role of Interstitial Pressure and Convection", Microvascular Research, vol. 37, pp. 77-104, (1989).

Helge Wiig, et al., "Interstitial fluid pressure in DMBA-induced rat mammary tumours", Scand. J. Clin. Lab. Invest., vol. 42, pp. 159-164, (1982).

Thomas P. Butler, et al., "Bulk Transfer of Fluid in the Interstitial Compartment of Mammary Tumors", Cancer Research, vol. 35, pp. 3084-3088, (Nov. 1975).

Intae Lee, et al., "Nicotinamide Can Lower Tumor Interstitial Fluid Pressure: Mechanistic and Therapeutic Implications", Cancer Research, vol. 52, pp. 3237-3240, (Jun. 1, 1992).

* cited by examiner

METHOD AND APPARATUS FOR DIAGNOSIS OF TUMOR ACTIVITY USING TUMOR INTERSTITIAL FLUID PRESSURE

SCOPE OF THE INVENTION

The present invention provides for the simplified measurement of the rate of fluid flux away from tumor tissues as an indication of tumor type, aggressiveness and/or treatment effectiveness, and more preferably as indicating relative differences between tumor interstitial fluid pressure and that of normal tissues.

BACKGROUND OF THE INVENTION

Despite remarkable strides in the treatment of solid cancers, such as those in the breast and prostate, many cancers remain resistant to treatment. As new therapies are developed and medicines become increasingly individualized, a need exists for effective and early diagnosis and/or predictor of treatment effectiveness or treatment response.

One physiological parameter which has demonstrated predictive value for tumor type or aggressiveness, and response to chemotherapy and/or radiotherapy is tumor interstitial fluid pressure (TIFP). Tumor interstitial fluid pressure (TIFP) is a physiological parameter that is elevated in aggressive tumors. TIFP decreases as tumors respond to treatments such as radiation therapy and chemotherapy. However at present, the clinical use of TIFP has been limited, as conventional techniques for TIFP measurement typically rely on biopsy procedures which are both invasive and which provide only point-measures.

The inventors have previously described a treatise on the basis for TIFP in the publication Liu L J, Brown S L, Ewing J R, Schlesinger M. "Phenomenological model of interstitial fluid pressure in solid tumor". Phys. Rev. E 2011; 83:021919, the disclosure of which is hereby incorporated herein by reference. The inventors have appreciated that the predictive value of TIFP, and its measurement, may advantageously be used in combination with tumor imaging methods, and more preferably, non-invasive imaging methods, in the diagnosis of tumor type and/or activity, and/or evaluating cancer treatment effectiveness and/or therapy response.

SUMMARY OF THE INVENTION

Elevated tumor interstitial fluid pressure (TIFP) derives from fluid accumulation within the tumor due to increased capillary permeability. Blood vessels become leaky in response to proteins secreted by tumor cells, once known as vascular permeability factor and more recently termed vascular endothelial growth factor, VEGF. Blood proteins permeate leaky vasculature, resulting in a loss of oncotic pressure gradient across the blood vessel wall. Fluid travels across the microvessel wall into interstitium as a consequence and contributes to elevated TIFP. High TIFP impairs lymphatic drainage and may contribute to tumor vasculature being abnormal. Tumor blood vessels are often contorted, dilated, and saccular, and may further be longer, larger in diameter, and denser than normal microvessels. As tumors grow, the abnormal vasculature limits the delivery of metabolites (nutrition and oxygen supply) and removal of wastes (such as lactic acid causing tumors to become acidic) to the tumor center. As a result, there are also regions in the center of the tumor devoid of microvessels. Consequently, some tumors with elevated TIFP develop a necrotic core surrounded by a perfused and growing rim.

The applicants have appreciated that TIFP will typically be either elevated throughout the tumor, or slightly reduced from the tumor periphery toward the tumor center, and drops to near zero (relative to normal tissue) at the tumor-normal tissue boundary.

The permeable tumor vasculature and pressure gradient between tumor and surrounding normal tissue allows for systemically administered imaging dyes, radioactive materials, or other contrast agents (hereafter collectively "contrast agents"), to distinguish tumors and cancerous cells from a patient's surrounding normal tissues. Such contrast agents are selected to allow for their concentration within the tumor, and their subsequent imaging to identify cancerous cells or tumors by suitable imaging apparatus. Such imaging apparatus may include without limitation magnetic resonance imaging (MRI) equipment, CT scanners, infrared scanners, sonographs or ultrasonic scanning equipment and/or conventional x-ray equipment.

It has been recognized that after the initial filling or exposure of a tumor with a suitable contrast agent, as a result of the leaky vasculature characteristics of selected tumor blood vessels, the size of the detected or imaged region of contrast will increase with time. In particular, the inventors have appreciated that due to fluid flux from the tumor into the patient's surrounding normal tissues, following the initial concentration and scanning of the contrast agent, the detected imaged area of the tumor will over time expand in a halo effect. The present invention provides in one possible embodiment, an apparatus and method for measuring the rate and/or extent of observed contrast-enhanced volume expansion and/or intensity change of the dyed tissue area as an indication of one or more of tumor type, tumor activity, treatment effectiveness and/or treatment response.

In a more preferred embodiment, the inventors propose a mathematical basis for measurement of TIFP distribution for use in tumor diagnosis and/or the assessment of treatment effectiveness is proposed.

In another embodiment, the invention provides a method and apparatus for use in measuring the rate of change in the contrast intensity and/or volume of dyed tumor tissues or cells as an indication TIFP.

A scanning apparatus, such as kinetic MRI, CT, x-ray or ultrasound imaging unit is preferably used to effect multiple images of a tumor in which a contrast agent has been localized over a selected time period to provide a measurement of TIFP. More preferably, the rate of change in the imaged area and/or contrast intensity of the dyed tissues is further used to assess tumor aggressiveness and as an early predictor of response to cancer therapy. In particular, it has been appreciated that following the marking of tumor or cancerous tissues by the initial localization of an imageable contrast agent, such as a radioactive dye therein, the rate of change in one or more of the area of the imaged marker or detected contrast agent and/or its change in volumetric area may be used to provide an indication of tumor interstitial fluid pressure (TIFP).

Accordingly, in one aspect, the present invention resides in a method for the diagnosis of tumor activity, a tumor property and/or tumor response in a region of interest in a patient, said region of interest including tumor and surrounding tissues, said method including, injecting a contrast agent which is detectable by an imaging apparatus as a marker into said patient, said contrast agent selected to initially concentrate in tumor tissues following injection, activating said imaging apparatus to obtain a first image of said region of interest at a first period of time, said first image including a first imaged marker representative of a distribution of said contrast agent in said tumor and surrounding tissues, activating said imaging apparatus to obtain a second image of said region of interest at a second subsequent period of time, said second image including a second imaged marker representative of a distribution of said contrast agent in said tumor and surrounding tissues, comparing at least one geometric property of the first imaged marker at said first period of time and said second imaged marker at said second period of time to identify the change in the distribution of the contrast agent in the region of interest between the first and second subsequent period of time.

In another aspect, the present invention resides in use of a system for the non-invasive diagnosis of tumor activity, tumor property and/or tumor response in a region of interest in a patient, said region of interest including tumor and surrounding tissues, said system including, an imaging apparatus for obtaining an image of said region of interest, an injectionable contrast agent selected to initially concentrate in tumor tissues in said region of interest, and when said region of interest is imaged by said imaging apparatus, said contrast agent appearing as an imaged marker for tumor cells, wherein said use, said imaging apparatus is activated to obtain a first image of said region of interest, to produce a first imaged marker representative of a distribution of said contrast agent in said tumor and surrounding tissues at a first period of time, and said imaging apparatus activated to obtain a second image of said region of interest, to produce a second imaged marker representative of a distribution of said contrast agent in said tumor and surrounding tissues at a second period of time, comparing at least one observed properties of said first imaged marker and said second imaged marker to assess the change in the distribution of the contrast agent in the region of interest.

In yet a further aspect, the present invention resides in a method of using an imaging apparatus for the non-invasive diagnosis of at least one of tumor activity, tumor property and tumor response in a patient region of interest including tumor and surrounding tissues, wherein following injection and concentration of an imaging apparatus detectable contrast agent in said region of interest, an initial period activating said imaging apparatus to obtain a first image of said region of interest, said first image including a first imaged marker representative a detected distribution of said contrast agent in said tumor and surrounding tissues at said initial period, and following said initial period activating said imaging apparatus to obtain at least one subsequent image of said region of interest, each subsequent image including a further imaged marker representative of a detected distribution of said contrast agent in said tumor and surrounding tissues at an associated subsequent period, comparing at least one of the areas and the volumes of the first imaged markers and one or more of the subsequent imaged markers to assess the rate of change in the distribution of the contrast agent in the region of interest.

BRIEF DESCRIPTION OF THE DRAWINGS

Reference may be had to the following detailed description taken together with the accompanying drawings in which.

DETAILED DESCRIPTION OF THE PREFERRED EMBODIMENTS

Figure 1:
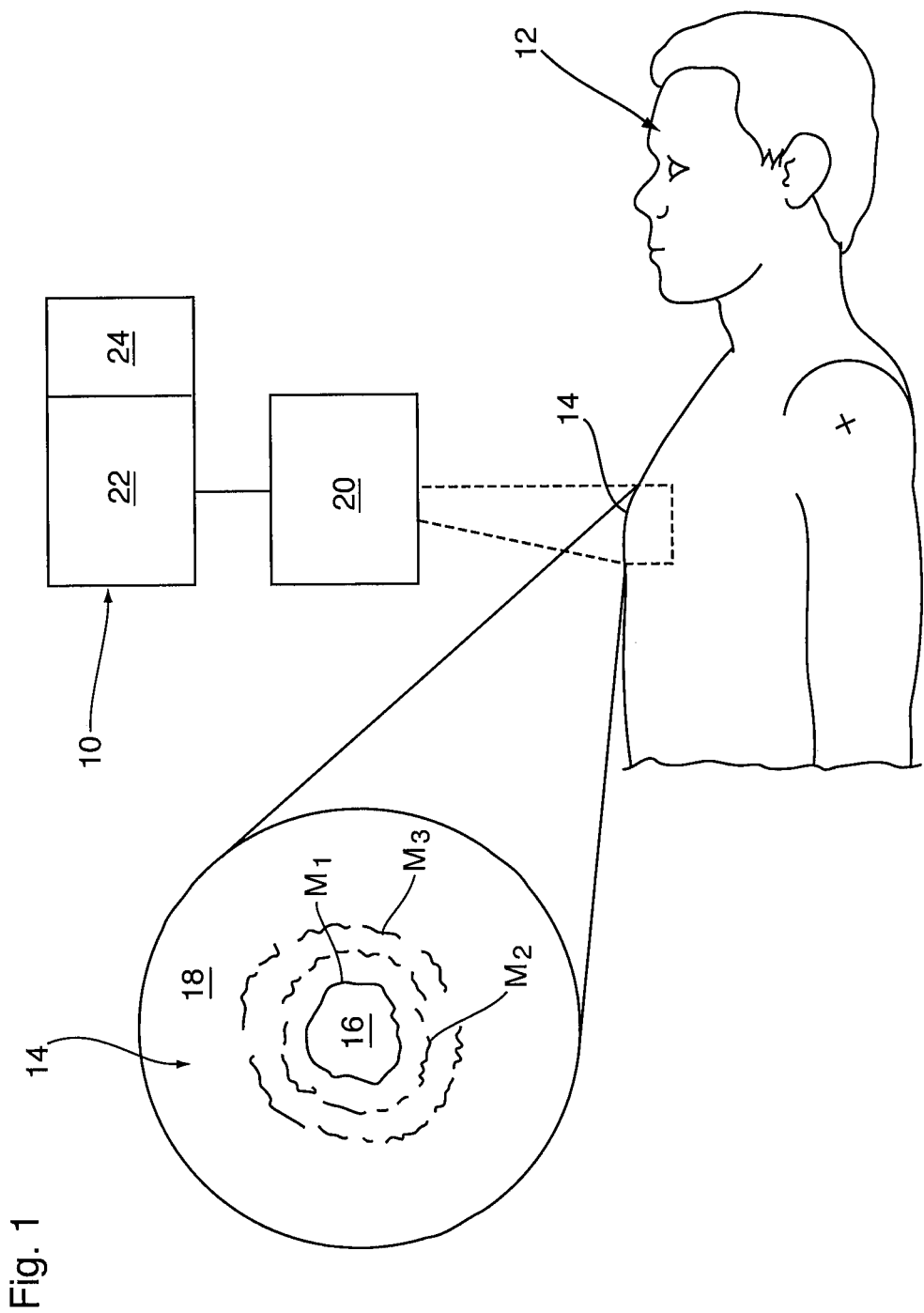
FIG. 1 shows schematically a system for use in the non-invasive diagnosis of tumor properties in accordance with a preferred embodiment of the invention.

Reference may be had to FIG. 1 which illustrates schematically an apparatus 10 for use in tumor identification and/or diagnosis in a patient 12. As will be described, the apparatus 10 is used in conjunction with a suitable contrast agent which is selected both for injection into the patient 12 to initially collect and concentrate within tumor or cancerous tissues (hereinafter collectively a tumor 16), and to be detectable by the apparatus 10 as a tumor marker to provide a detectable or imaged marker M thereof. In a preferred embodiment, the apparatus 10 is provided with an electromagnetic radiation (EMR) source 20 which is operable to produce optical images of a region of interest 14 in the patient 12, and which is selected as a site likely including a solid tumor 16 together with its surrounding tissue 18.

The EMR source 20 is preferably selected as an MRI apparatus which is operable to detect and output an image or data (hereinafter collectively referred to as an image) of the injected contrast agent. The EMR source 20 is operated by way of a processor/controller 22 having memory 24 to scan and obtain over time periods $t_1, t_2, t_3, \ldots t_n$, multiple optical images of the region of interest 14.

In use, the contrast agent is initially injected into the patient 12, and a first period of time ($t_1$) is permitted to pass which is selected to achieve the optimum concentration of the contrast agent within the tumor 16. Typically the first time period $t_1$ is selected at between about 0.5 and 15 minutes, however, longer or shorter periods of time may be necessary depending on the tumor and/or contrast agent type, and the loci of the injection.

Following the passage of time $t_1$ after initial contrast agent injection into the patient 12, the processor/controller 22 is used to activate the EMR source 20 to obtain and store in the memory 24 multiple images of the tumor 16 and surrounding tissue 18 over a selected timeframe. Most preferably images are obtained at predetermined and/or measured intervals between 0.5 and 60 minutes apart, and most preferably between about 3 and 15 minutes following the initial contrast agent injection. In this manner the apparatus 10 produces multiple images of the region of interest 14, which show the concentration and dispersion over time of the contrast agent as an imaged marker $M_1, M_2, M_3, \ldots M_n$ at each respective time $t_1, t_2, t_3, \ldots t_n$.

The processor/controller 22 is then activated to optically analyze in each obtained image, a geometric property, and preferably an area of the imaged marker $M_1, M_2, M_3 \ldots M_n$ (as shown by the detected contrast agent), and to further calculate the rate of the change in marker area over time. The rate at which the detected contrast area is observed to expand is then correlated either by the processor/controller 22 with data prestored in the memory 24 or by a medical professional with predetermined anticipated dispersion or expansion rates for benign and malignant classes of like tumors, to provide an indication of tumor type and/or activity.

Whilst a simplified embodiment of the invention describes the apparatus 10 as including an imaging apparatus such as an EMR source 20 operable to provide images showing the change in area of the scanned imaged markers $M_1, M_2, M_3 \ldots M_n$ (or detected enhanced portion of the images), more preferably the imaging apparatus 10 is provided with three-dimensional scanning capabilities. In such a configuration, the EMR source 20 is operable to obtain three-dimensional images of the area of interest 14 including the tumor 16 and surrounding tissue 18. The processor/controller 22 is operable to calculate the rate of change in the volume area of each imaged marker $M_1, M_2, M_3 \ldots M_n$ by comparing the geometry of the contrast-enhanced tissues shown in successively scanned images of the region of interest 14. The imaged markers M are used to calculate the rate of volume expansion of the contrast-enhanced region highlighted by the contrast agent over time, may thus be used to calculate fluid flux in or from the tumor 16 and/or tumor interstitial fluid pressure.

Scientific Principle

Without being bound by a specific scientific theory, it is understood that tumors are provided with distinct regions including a core, with or without necrotic tissue, having radius $r_n$ and a well perfused periphery characterized by leaky vasculature. As a tumor grows, the tumor center enlarges and the periphery remains approximately the same width. This is the classical "orange rind model" of a tumor.

The pressure profile is from high (relative to normal tissue) interstitial fluid pressure, IFP, in tumor core and low IFP in surrounding normal tissue. TIFP results from fluid collecting in the interstitial spaces surrounding leaky vasculature. In the surrounding normal tissues, the fluid is carried away by lymphatics or by the processes of convection and/or diffusion. Within the tumor the lymphatics system is impaired. Consequently, a pressure gradient exists in the intermediary region between tumor core and tumor periphery.

The net fluid flux $J_s$ that leaks from tumor blood vessels follows Starling's law, the relationship connecting TIFP, p, with the surface area, A, of the blood vessels, the vascular fluid pressure, $p_v$, the osmotic pressure difference, $\pi_v$-$\pi$, between the plasma in the blood vessel and interstitial fluid, the osmotic reflection coefficient, σ, and the hydraulic conductivity, L, of the blood vessel. The net driving pressure is defined as $(p_v$-$p)$-$\sigma(\pi_v$-$\pi)$. Starling's law defines the net fluid flux $J_s$ as proportional to the product of the surface area A of the blood vessels and the net driving pressure. The proportionality coefficient is the hydraulic conductivity L.

In a tumor, L and A are much greater, than those in the normal tissue, whereas $\pi_v$-$\pi$ is smaller. This makes the net fluid flux $J_s$ in a tumor much greater than that in normal tissue. If both outer and inner spherical surfaces of the vascularized region are closed and no fluid can flow out, the net fluid flux is zero at a steady state. Further, IFP in this region is at maximum value, which is expressed as the difference between the vascular fluid pressure $p_v$ and $\sigma(\pi_v$-$\pi)$—the product of the osmotic reflection coefficient σ and the osmotic pressure difference $\pi_v$-$\pi$ between the plasma and interstitial fluid. Once TIFP reaches this value, no fluid flows out from blood vessels. When there are openings on each spherical surface of the vascularized region, the pressure will be modified from the two surfaces to the central area of that region. With the openings increasing, the pressure decreases. In the maximum pressure area, fluid remains stationary since there is no pressure difference. The maximum pressure region becomes narrower when the openings become larger. Correspondingly, the flow rate across these two surfaces becomes larger. The maximum pressure region will narrow down to a point when the openings widen to a critical value. If the openings continue to increase, then the highest pressure $p_0$ becomes smaller than $p_m$. The bigger the openings are, the smaller the $p_0$. The maximum value of IFP at steady state is between 0 and $p_m$. The exact value $p_0$ depends on the conditions, such as the pressure $p_v$ inside blood vessels, the osmotic pressure difference $\pi_v$-$\pi$ between the plasma and interstitial fluid, the lymphatic drainage ability and fluid flow rate from the openings. The pressure at the surface of necrotic core depends on the conditions within the necrotic core $p_{in}$, and the pressure at the periphery of a tumor depends on the conditions of the environment.

TIFP in the Central Area

TIFP variation in the central area depends on $p_0$, the pressure barrier, and the fluid conditions in the region. Initially, pressure in the necrotic core area is smaller than the pressure $p_0$. The leaked fluid flows into this area. Since drainage (lymphatics) does not readily occur, more and more fluid accumulates within the core, gradually increasing the pressure in the region and reaching $p_0$ after the fluid fills up the entire area. Once $p_0$ is reached, no more fluid can flow into the area, with the central area maintaining a constant pressure $p_0$, and which is as high as that of the pressure barrier. With the central area filled with fluids, all leaked fluid flows to the outside. The pressure in the necrotic core thus should be the same as that at the surface, $r=r_n$ where the fluid flows in. The relation between IFP and the fluid velocity is constrained by Darcy's law, which states that the fluid velocity is proportional to the negative gradient of TIFP. The proportionality coefficient K is defined as the hydraulic conductivity of the interstitium. The more fluid accumulates in this region, the higher the pressure will be. Correspondingly, the pressure difference between $p_0$ and $p(r_n)$ becomes smaller and smaller. Therefore, the fluid velocity across the surface ($r=r_n$) of the necrotic core will also be smaller. When $p(r_n)$ equals to $p_0$, the pressure difference is zero so no more fluid flows in. Assuming the radius that corresponds to the pressure barrier $p_0$ is $r_0$, the whole region inside $r_0$ reaches pressure $p_0$. The pressure difference $p_0$-$p_{in}(t)$ decreases from $p_0$-$p_{in}(0)$ exponentially with time. This TIFP variation may also be applied to a contrast agent if one is used. At steady state, TIFP in the region within $r_0$ is uniformly $p_0$. The exact value of $p_0$, which is between 0 and $p_m$, will depend on the conditions at the periphery of the tumor.

TIFP in the Periphery

In the periphery, the difference between the tumor radius R and $r_0$ (which corresponds to the pressure barrier $p_0$) is small. Darcy's law gives an approximate linear relationship between the fluid velocity change and IFP change from $r_0$ to R. Since fluid velocity $u(r_0)$ at $r_0$ is zero, the fluid velocity u(R) at the periphery is proportional to the ratio of the IFP variation $p_0$-p(R) to the difference R-$r_0$. This relationship connects $p_0$ with the fluid velocity u(R) and IFP p(R), which is balanced with the IFP of the environment.

TIFP Measurement

The value of $p_0$ may be determined by measuring p(R) and u(R). As such, u(R) may be measured non-invasively using a contrast enhanced imaging modality, as by way of non-limiting example, computed tomography (CT) or magnetic resonance imaging (MRI), or ultrasound (US) either of these together with a suitable contrast agent.

TIFP in the periphery and intermediary region can be determined based on corresponding environmental conditions. When fluid velocity at tumor periphery is greater than a critical fluid velocity $u_c(R)$, p(R) is zero; otherwise, p(R) is greater than zero. For instance, where for example $p_0$=15 mmHg, K=4.13×10$^{-8}$ cm$^2$/mm HgSec, $r_0$=0.9 cm, R=1.0 cm, $u_c(R)$=0.124 μm/sec or 0.5 mm/hour, which corresponds to the results for isolated tumors, as for example is described in Baxter L T, Jain R K. "Transport of fluid and macromolecules in tumors I. Role of interstitial pressure and convection". *Microvasc Res* 1989; 37(1): 77-104, the disclosure of which is incorporated herein by reference. Previous authors have estimated that fluid velocity at the periphery of isolated tumors is 0.13-0.2 μm/sec (see Baxter above). There is a critical flow rate $Q_c$, which is defined as $4\pi R^2 u_c(R)$, coinciding with the critical fluid velocity, and which for a tumor with radius R=1.0 cm, $Q_c$=1.56×10$^{-4}$ ml/sec. TIFP p(R) at the periphery of the tumor is zero if the lymphatic drainage's ability is large enough to ensure the maximum drainage (i.e. $Q_m$ is greater than $Q_c$). When the drainage ability $Q_m$ is smaller than the critical flow rate $Q_c$, the drainage ability of the tumor is small so that TIFP at the periphery will be high. When the TIFP at the periphery is too high for the given conditions, the tumor must find a way to release the pressure by creating channels that connect with normal tissue. Here the pressure release may result in the break of the normal structure at the interface or make it complicated. $Q_c$ may be a factor for determining whether it is an isolated or embedded tumor. In this case, the fluid flux Q at a tumor edge $4\pi R^2 u(R)$ is greater than the drainage ability $Q_m$, but smaller than the critical flow rate $Q_c$. Some fluid crosses over the edge (r=R) and flows into the normal tissue. Lymphatics are plenty and functional in normal tissue, so some fluid is drained away. Similar to the Starling's law, the net fluid flux drained from the lymphatics is proportional to the surface area $A(r_m)$ and the pressure difference between TIFP and the pressure $p_L$ in lymphatics. The proportionality coefficient is $L_L$, which is defined as the hydraulic conductivity of lymphatics. The $r_m$ is the maximum radius of fluid that the tumor can spread. The maximum radius corresponds to the radius from which the pressure becomes the same as the pressure of the normal tissue. When balanced, the pressure $p_L$ in lymphatics should be the same as that in the environment $p_\infty$. $A_L(r_m)$ is the total surface area of the lymphatics within radius $r_m$. At steady state, the radius is a fixed value; therefore, the $A_L(r_m)$ is fixed. Since fluid does not tend to collect outside the tumor, the total fluid flux across the tumor edge should be conserved. Combined with Darcy's law, the distribution of TIFP outside the tumor may be determined. In particular, TIFP in the region from $r_0$ to R can be determined by considering the continuity conditions.

Time Dependent TIFP

Besides being spatially different, the net fluid flux in a tumor is time dependent. In normal tissues with functional vasculature and lymphatics, the interstitial fluid is balanced, that is, all capillaries have the same L,σ, pressure difference $p_v$-p and osmotic pressure difference $\pi_v$-π. In contrast, in tumor tissues, the capillaries are abnormal and lymphatics are absent. Consequently, L, σ and $\pi_v$-π are not uniform but rather heterogeneous, though the $p_v$ may stay the same. The total fluid flux at time t is the sum of fluid flux from different capillaries at time t. Permeable microvessels have an osmotic pressure difference $\pi_v$-π approaching zero. Leaky capillaries near the tumor/normal tissue boundary have conductivity greater than that of the capillaries in the central region. The osmotic pressure difference may possibly also be smaller in this area. The total fluid flux near the tumor edge is therefore expected to be much greater than that in the central area, assuming that the total fluid flux near the edge represents the total fluid flux of the tumor. In this narrow region, the value of the different vascular parameters is homogeneous.

Noninvasive Measurement

The distribution of TIFP was derived under steady state conditions based on the rate of contrast agent flux from the tumor into the normal tissue as a function of time.

A minimally-invasive measurement of TIFP is possible based on the aforementioned model. An exemplary approach was an MRI protocol which could be performed as a modification of current imaging practices.

Figure 2:
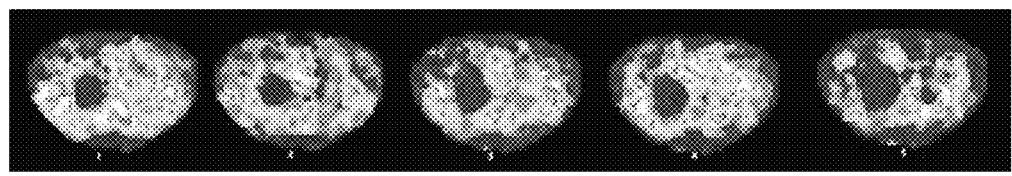
FIG. 2 shows an imaged tumor illustrating the change in the detected area of contrast agent over an elapsed period of three minutes to fifteen minutes following agent injection.

Often MRI diagnostic tests use a vascular contrast agent to delineate a suspicious mass prior to a biopsy procedure. Depending on the imaging sequence used, the contrasted volume of tissues in which the contrast agent is concentrated may vary and in fact appear to increase with duration (measured in minutes) after its initial administration. This phenomenon is shown in FIG. 2. In particular, FIG. 2 illustrates the consequence of high TIFP on contrast agent kinetics in a rat 9L cerebral glioma acquired using a 7 Tesla MRI. The five panels illustrate ratio images of T2* to T1 relaxivities, so called, "Gamma-2 images", taken at minute 3 through minute 15 following the injection of the contrast agent (Gadomer™) and which from left to right were acquired at 2.5 minute intervals. The movement of the contrast agent wave front (blue circular region) in normal tissue is clearly visualized across this time period. FIG. 2 shows a pulse sequence of five images of a tumor region in which the contrast agent is concentrated and image analysis technique sensitive to the presence of contrast. The result shown in FIG. 2 reflect a contrast agent wave front which appears to increase in volume as a function of time, as the contrast agent streams outwardly at a velocity u(R) from initially concentrated within tumor and into surrounding normal tissue. The rate of contrast agent flux is proportional to the TIFP relative to that of surrounding normal tissue (i.e. usually near zero).

Though a spherical three-dimensional model was used in the clinical testing, the invention is not limited to the specific geometry. Contrast agent flux at irregular boundaries can be modeled at various gradient directions perpendicular to the tumor boundary. However, as an approximation, at a distance away from most tumors, a simple spherical model may be advantageously adequately approximate the contrast agent kinetics and movement.

The present invention is suitable for use with any imaging modality capable of monitoring the dynamics of a contrast agent to determine TIFP, including MRI, CT, US, PET and SPECT.

The current technique further may also advantageously be used to augment image-guided radiation therapy, since regions of a tumor identified to be more aggressive than other regions, may be isolated and treated accordingly. The present invention thus shows promise as a simple, new imaging apparatus and method which could be rapidly implemented on a variety of clinical machines and has the potential to identify or predict tumor response to cancer treatment.

Although the detailed description describes the use of Gadomer™ as the contrast agent used in tumor imaging, the invention is not so limited. It is to be appreciated that the present invention is also contemplated for a use with a variety of different types of radioactive and nonradioactive contrast agents, including, without restriction, radioactive iodine dyes, blue dye, Patentblau V, iron-based contrast agents, mircobubble contrast agents and phosphorescent contrast agents selected to allow dye loading within cancer tissues or tumors.

While the preferred embodiment of the invention describes the apparatus 10 as operable to calculate the rate of expansion of the area or volume of the imaged marker (contrast-enhanced tissue region), the invention is not so limited. In an alternate construction, the processor/controller 22 may be used to measure and output the rate of change of the intensity of part or all of the imaged markers over time. Such a change in contrast would be extrapolated as showing the dissipation and migration of the contrast agent from its initial concentration within the tumor 16.

While the detailed description describes and illustrates various preferred embodiments, the invention is not limited strictly to the precise embodiments which are disclosed. Modifications and variations will now occur to persons skilled in the art. For a definition of the invention, reference may be had to the appended claims.

We claim:

1. A method for the diagnosis of tumor activity and/or a tumor property in a region of interest in a patient, said region of interest including tumor and surrounding tissues, said method including, injecting a contrast agent which is detectable by an imaging apparatus as a marker into said patient, said contrast agent selected to initially concentrate in tumor tissues following injection, activating said imaging apparatus to obtain a first image of said region of interest at a first period of time, said first image including a first imaged marker representative of a distribution of said contrast agent in said tumor and surrounding tissues, activating said imaging apparatus to obtain a second image of said region of interest at a second subsequent period of time, said second image including a second imaged marker representative of a distribution of said contrast agent in said tumor and surrounding tissues, comparing at least one geometric property of the first imaged marker at said first period of time and said second imaged marker at said second period of time to identify a rate of change in the distribution of the contrast agent in the region of interest between the first and second subsequent period of time, and correlating the rate of change in the distribution of the contrast agent to at least one of tumor interstitial fluid pressure and tumor fluid flux, and wherein the diagnosis of tumor activity comprises classifying said tumor as a benign tumor or a malignant tumor based on the rate of change in distribution of the contrast agent.

2. The method as claimed in claim 1 further wherein the at least one geometric property includes an area of the first and second imaged markers.

3. The method as claimed in claim 1 further wherein the at least one geometric property includes a measured or approximate volume of the first and second imaged markers.

4. The method as claimed in claim 1 further comprising following said step of obtaining said second image, obtaining at least one further image of said region of interest, each further image including an associated further imaged marker representative of a distribution of said contrast agent in said tumor and surrounding tissues at a further time period, and comparing a geometric property of the further imaged markers with one said geometric property of said first imaged marker and/or said second imaged marker to identify the rate of change in distribution of the contrast agent between at least one of the first and second subsequent period of time and the further time period.

5. The method as claimed in claim 4 further wherein the at least one geometric property includes a measured or approximate volume of the first and second imaged markers.

6. The method as claimed in claim 5 wherein, said first period of time being selected at between about 0.5 to 15 minutes following said step of injection, and said second subsequent period of time being selected as between about 2 to 25 minutes following said first period of time.

7. The method as claimed in claim 1 for the diagnosis of said tumor property, wherein the tumor property is selected from the group consisting of tumor vasculature permeability and tumor pressure gradient.

8. The method of claim 1 wherein said imaging apparatus comprises a non-invasive imaging apparatus selected from the group consisting of an MRI Scanner, an EM scanner, a CT scanner, and an ultrasound scanner.

9. Use of a system for the non-invasive diagnosis of tumor activity and/or tumor property in a region of interest in a patient, said region of interest including tumor and surrounding tissues, said system including, an imaging apparatus for obtaining an image of said region of interest, an injectionable contrast agent selected to initially concentrate in tumor tissues in said region of interest, and when said region of interest is imaged by said imaging apparatus, said contrast agent appearing as an imaged marker for tumor cells, wherein said use, after injecting said contrast agent concentrating in said tumor, activating said imaging apparatus to obtain a first image of said region of interest, to produce a first imaged marker representative of a distribution of said contrast agent in said tumor and surrounding tissues at a first period of time, and activating said imaging apparatus to obtain a second image of said region of interest, to produce a second imaged marker representative of a distribution of said contrast agent in said tumor and surrounding tissues at a second period of time, comparing at least one observed property of said first imaged marker and said second imaged marker to assess a rate of change in the distribution of the contrast agent in the region of interest, wherein the observed property is a geometric property, and further correlating the rate of change in said geometric property over time to at least one of an interstitial fluid pressure of said tumor, a vasculature permeability of said tumor and a tumor pressure gradient, and wherein the diagnosis of tumor activity comprises classifying said tumor as a benign tumor or a malignant tumor based on the rate of change in distribution of the contrast agent.

10. The use as claimed in claim 9 wherein the geometric property comprises an area of the produced imaged markers.

11. The use as claimed in claim 9 wherein the geometric property comprises a volume of the produced imaged markers.

12. The use as claimed in claim 9 wherein said second period of time is selected at between about 0.5 to 60 minutes, and preferably between about 1 and 15 minutes following the first period of time.

13. The use as claimed in claim 9 wherein the tumor property is selected from the group consisting of tumor vasculature permeability and tumor pressure gradient.

14. The use as claimed in claim 9 wherein the imaging apparatus is selected from the group consisting of an MRI apparatus and an EM apparatus.

15. A method of using an imaging apparatus for the non-invasive diagnosis of at least one of tumor activity and tumor property in a patient region of interest including tumor and surrounding tissues, wherein following injection and concentration of an imaging apparatus detectable contrast agent in said region of interest, at an initial period activating said imaging apparatus to obtain a first image of said region of interest, said first image including a first imaged marker representative a detected distribution of said contrast agent in said tumor and surrounding tissues at said initial period, and following said initial period activating said imaging apparatus to obtain at least one subsequent image of said region of interest, each subsequent image including a subsequent imaged marker representative of a detected distribution of said contrast agent in said tumor and surrounding tissues at an associated subsequent period, comparing at least one of an area and a volume of the first imaged marker and one or more of an area and a volume of the subsequent imaged markers to assess a rate of change relative to time in the distribution of the contrast agent in the region of interest, and correlating the rate of change in the distribution of the contrast agent to at least one of tumor internal fluid pressure and tumor fluid flux, and wherein the diagnosis of tumor activity comprises classifying said tumor as a benign tumor or a malignant tumor based on the rate of change in distribution of the contrast agent.

16. The method as claimed in claim 15 wherein the tumor property is selected from the group consisting of tumor vasculature permeability and tumor pressure gradient.

17. The method as claimed in claim 15 wherein the imaging apparatus is selected from the group consisting of an MRI apparatus, an EM apparatus, an ultrasound apparatus and an x-ray apparatus.

18. The method as claimed in claim 15 wherein,
said initial period being selected at between about 0.5 to 15 minutes following injection of the contrast agent, and
said subsequent period being selected at between about 2 to 25 minutes following said initial period.

* * * * *